US006596904B1

(12) United States Patent
Dunn et al.

(10) Patent No.: US 6,596,904 B1
(45) Date of Patent: Jul. 22, 2003

(54) PROCESS FOR PRODUCING IOVERSOL

(75) Inventors: Thomas Jeffrey Dunn, Cedar Hill, MO (US); David H. White, Ballwin, MO (US); Mills Thomas Kneller, University City, MO (US); Michelle M. Jones, Grover, MO (US); Narciso Ocampo Doran, III, Bridgeton, MO (US); Allan R. Bailey, Manchester, MO (US)

(73) Assignee: Mallinc Krodt Inc, St Louis, MO (US)

( * ) Notice: Subject to any disclaimer, the term of this patent is extended or adjusted under 35 U.S.C. 154(b) by 1372 days.

(21) Appl. No.: 08/593,775

(22) Filed: Jan. 29, 1996

(51) Int. Cl.$^7$ ...................... C07C 233/05; C07C 233/65
(52) U.S. Cl. ...................... 564/153; 424/9.454
(58) Field of Search ...................... 546/153; 424/9.454

(56) References Cited

U.S. PATENT DOCUMENTS 4,396,598 A * 8/1983 Lin ............................... 424/5
4,997,983 A * 3/1991 McCarthy .................... 564/153
5,177,261 A * 1/1993 McCarthy et al. ........... 564/153

* cited by examiner

*Primary Examiner*—Shailendra Kumar

(57) ABSTRACT

The present invention discloses a new process for producing ioversol (marketed as OPTIRAY®) comprising:

(a) reacting 5-amino-N,N'-bis(2,3-dihydroxypropyl)-2,4,6-triiodoisopthalamide with chloroacetyl chloride in a polar aprotic solvent or combinations thereof to produce N,N'-bis[2,3-di(2-chloroacetoxy)propyl]-5-(2-chloroacetamido)-2,4,6-triiodoisophthalamide;

(b) reacting the product of (a) with a base to produce N,N'-bis(2,3-dihydroxypropyl)-5-(2-chloroacetamido)-2,4,6-triiodoisopthalamide;

(c) reacting the product of (b) with an alkylating agent capable of producing a hydroxyethylated product in the presence of a base and water to produce N,N'-bis(2,3-dihydroxypropyl)-5-[N-(2-hydroxyethyl) (2-chloroacetamido)]-2,4,6-triiodoisopthalamide; and (d) reacting the product of (c) in water and acetate ions to produce ioversol.

10 Claims, No Drawings

PROCESS FOR PRODUCING IOVERSOL

FIELD OF THE INVENTION

This invention is in the field of imaging. In particular, the invention relates to X-ray imaging. And most particularly, the invention relates to a new process for obtaining ioversol.

BACKGROUND OF THE INVENTION

This invention relates to N,N'-bis(2,3-dihydroxypropyl)-5-N-(2-hydroxyethyl)glycolamido-2,4,6-triiodoisopthalamide (ioversol).

Ioversol is commonly used as an X-ray contrast agent. The agent may be used in various radiographic procedures including those involving cardiography, coronary arteriography, aortography, cerebral and peripheral angiography, arthroglraphy, intravenous pyelography and urography as well as myelograpihy.

The present commercial manufacture of ioversol proceeds in four steps from bis(2,3-dihydroxypropyl)-2,4,6-triiodo-5-aminoisophthalamide to crude ioversol product, which product is subsequently purified. This conversion utilizes two expensive raw materials, acetoxyacetyl chloride (AAC) and bromoethylacetate (BEA), which together contribute to greater than 25% of the final product material cost. Additionally, the present commercial manufacturing process requires the use of several expensive, environmentally undesirable and/or reactive solvents such as 1,1,2-trichloroethane (TCE), dimethylsulfoxide (DMSO) and amylacetate. Each of these solvents have been particularly troublesome in manufacturing due to difficulties in recovery and other operational difficulties. TCE, in particular, is a chlorinated solvent of considerable concern in manufacturing. Thus, there exists a need for an improved process for then manufacture of ioversol which incorporates less expensive and more environmentally suitable raw materials.

SUMMARY OF THE INVENTION

The present invention provides a new process for producing ioversol (marketed in final dosage form as OPTIRAY®) comprising:
(a) reacting 5-amino-N,N'-bis(2,3-dihydroxypropyl)-2,4,6-triiodoisopthalamide with chloroacetyl chloride in a polar aprotic solvent or combinations thereof to produce N,N'-bis[2,3-di(2-chloroacetoxy)propyl]-5-(2-chloroacetamido)-2,4,6-triiodoisophthalamide;
(b) reacting the product of (a) with a base to produce N,N'-bis(2,3-dihydroxypropyl)-5-(2-chloroacetamido)-2,4,6-triiodoisopthalamide;
(c) reacting the product of (b) with an alkylating agent capable of producing a hydroxyethylated product in the presence of a base and water to produce N,N'-bis(2,3-dihydroxypropyl)-5-[N-(2-hydroxyethyl)(2-chloroacetamido)]-2,4,6-triiodoisopthalamide; and
(d) reacting the product of (c) in water and acetate ions to produce ioversol.

The new synthetic route replaces the high cost AAC and BEA components with chloroacetylchloride (CAC) and an alkylating agent which is capable of producing a hydroxyethylated product, respectively, thus reducing the introduction of these components to a more elementary and far less expensive archetype. Further, except for a small quantity of the polar aprotic solvent dimethylacetamide (DMAC) utilized in the initial step, the remaining reactions are conducted in an aqueous reaction medium, eliminating TCE, DMSO and amyl acetate and their corresponding costs and environmental difficulties.

DETAILED DESCRIPTION

The current process for producing ioversol is generally depicted in Table 1 below:

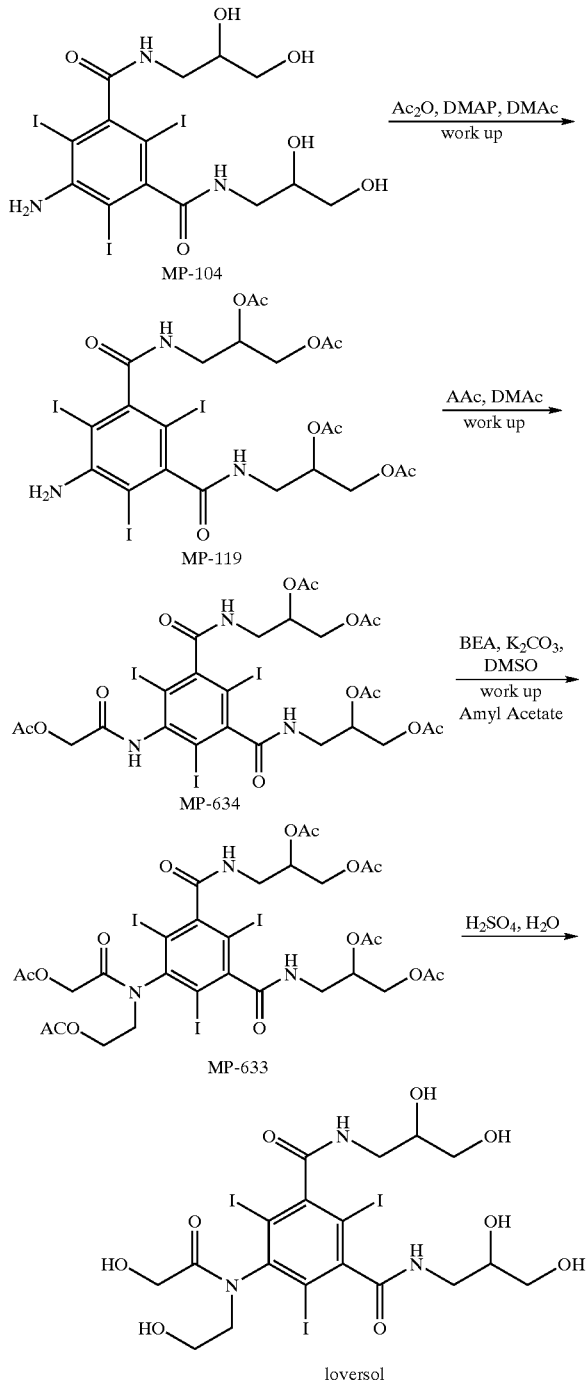

The current general procedure for producing ioversol is as follows:

STEP 1

Preparation of 5-Amino-N,N'-bis(2,3-diacetoxypropyl)-2,4,6-triiodoisophthalamide 5-Amino-N,N'-bis (2,3-dihydroxpropyl)-2,4,6-triiodoisophthalamide is dissolved in N,N-diomethylacetamide and acetylated with acetic anhydride, using 4-dimethylaminopyridine as a catalyst, to produce 5-amino-N,N'-bis(2,3-diacetoxypropyl)-2,4,6-triiodoisophthalamide. Upon completion of the reactions the mixture is diluted with 1,1,2-trichloroethane and washed with aqueous sodium carbonate and aqueous sodium chloride solutions to remove acetic acid, which is the by-product of the reaction. The resulting 1,1,2-trichloroethane solution of the product is used in STEP #2.

STEP 2

Preparation of 5-Acetoxyacetamido-N,N'-bis(2,3-diacetoxypropyl)-2,4,6-triiodoisophthalamide Most of the solvent (1,1,2-trichloroethane) is distilled from the solution of 5-amino-N,N'bis(2,3-diacetoxypropyl)-2,4,6-triiodoisophthalamide prepared in STEP #1. The reaction solvent, N,N-dimethylacetamide, is added. Excess acetoxyacetyl chloride is added and the reaction mixture is stirred at ca. 40° C. until the reaction is completed. 5-Acetoxyacetamido-N,N'-bis(2,3-diacetoxypropyl)-2,4,6-triiodoisophthalamide is formed. 1,1,2-trichloroethane is added to dilute the reaction mixture and the solution is washed with aqueous sodium bicarbonate and aqueous sodium chloride solutions to remove acetoxyacetic acid and other by-products. The resulting organic layer which contains the reaction product is used in the next step.

STEP 3

Preparation of 5-[N-(2-Acetoxyethyl) acetoxyacetamido]-N, N'-bis(2,3-diacetoxypropyl)-2,4,6-triiodoisophthalamide Solvent (1,1,2-trichloroethane) is distilled from the solution of 5-acetoxyacetamido-N,N'-bis(2,3-diacetoxypropyl)-2,4,6-triiodoisophthalamide prepared in STEP #2. Dimethyl sulfoxide is added as the reaction solvent. Potassium carbonate and 2-bromoethyl acetate are added and the mixture is stirred for ca. 10 hours at ca. 40° C. to complete the reaction to form 5-[N-(2-acetoxyethyl)acetoxyacetamido]-N,N'-bis(2,3-diacetoxypropyl)-2,4,6-triiodoisophthalamide. After the reaction is completed, 1,1,2-trichloroethane is added to dilute the mixture. To remove the inorganic salts and dimethyl sulfoxide in the medium, the mixture is washed once with deionized water, and twice with aqueous sodium chloride solution. The organic layer, which contains the product, is then distilled to remove the solvent and the residue is dissolved in amyl acetate while the mixture is still hot. The mixture is then cooled and stirred continuously to complete the crystallization. The reaction product is collected and dried. After testing, it is used in STEP #4 to prepare crude ioversol aqueous solution.

STEP 4

Preparation of N,N'-bis(2,3-dihydroxypropyl)-5-[N-(2-hydroxyethyl)glycolamido]-2,4,6-triiodoisophthalamide, (Crude ioversol Aqueous Solution)

5-[N-(2-Acetoxyethyl)acetoxyacetamido]-N,N'bis(2,3-diacetoxypropy)-2,4,6-triiodoisophthalamide solids are slurried in hot water containing a catalytic quantity of sulfuric acid. The solid gradually dissolves as it is heated with the steam on the jacket. The material is hydrolyzed to produce crude ioversol and acetic acid as a by-product. To remove the acetic acid, clean steam is sparged into the reactor. The solution volume is maintained constant by adding deionized water during the reaction and acetic acid removal. The reaction is tested for completeness of hydrolysis and for the removal of acetic acid.

The solution which contains ioversol, (crude ioversol aqueous solution) is cooled and utilized in subsequent purification steps.

The process of the invention for producing ioversol is depicted in Table 2 below:

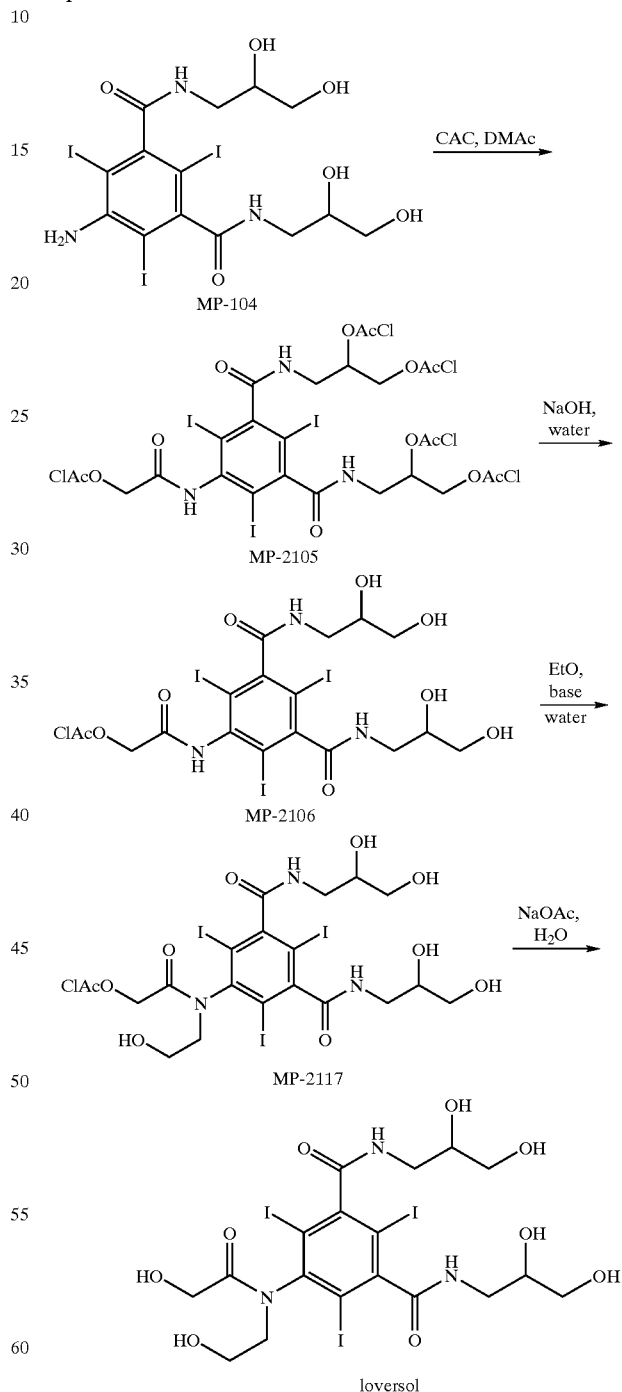

The general procedure for the process of the invention involves reacting 5-amino-N,N'-bis(2,3-dihydroxypropyl)-2,4,6-triiodoisophthalamide with chloroacetyl chloride in a polar aprotic solvent.

The general procedure for the process of the invention involves reacting 5-amino-N,N'-bis(2,3-dihydroxypropyl)-2,4,6-triiodoisophthalamide with N,N-dimethylacetamide and chloroacetyl chloride. The resulting product is hydrolyzed with a base (such as sodium hydroxide). A homogeneous solution is obtained by adding water. Precipitation is affected to yield N,N'-bis(2,3-dihydroxypropyl)-5-(2-chloroacetamido)-2,4,6-triiodoisophthalamide. Alternately, 5-amino-N,N'-bis(2,3-dihydroxypropyl)-2,4,6-triiodoisophthalamide is reacted with N,N-dimethylacetamide, acetonitrile, and chloroacetyl chloride. The resulting product is hydrolyzed with a base. A homogeneous solution is obtained by adding water. Precipitation is affected to yield N,N'-bis(2,3-dihydroxypropyl)-5-(2-chloroacetamido)-2,4,6-triiodoisophthalamide. This product is combined with an aqueous base and deionized water. 2-Chloroethanol is added followed by heating. The addition of hydrochloric acid yields N,N'-bis(2,3-dihydroxypropyl)-5-[N-(2-hydroxyethyl)(2-chloroacetamido)]-2,4,6-triiodoisophthalamide. Alternately, N,N'-bis(2,3-dihydroxypropyl)-5-(2-chloroacetamido)-2,4,6-triiodoisophthalamide plus metal halide and deionized water are combined. Ethylene oxide is added followed by heating. The addition of hydrochloric acid yields N,N'-bis(2,3-dihydroxypropyl)-5-[N-(2-hydroxyethyl)(2-chloroacetamido)]-2,4,6-triiodoisophthalamide. This product is suspended in water with acetate ions and hydrochloric acid added. This suspended solution can take place at or above atmospheric pressure. Generally about 1 to about 2 atmospheres above atmospheric pressure is used. After adding aqueous sodium hydroxide to, maintain the pH, the reaction yields N,N'-bis(2,3-dihydroxypropyl)-5-N-(2-hydroxyethyl)glycolamido-2,4,6-triiodoisopthalamide. Finally, salts and low molecular weight impurities are removed.

Polar aprotic solvents for use with the invention include dimethylacetamide, acetonitrile, dimethylsulfoxide, dimethylformamide, tetrahydrofuran, dimethoxyethane, dioxane, or combinations thereof. Suitable bases for use with the water include sodium hydroxide, lithium hydroxide, ammonium hydroxide, potassium hydroxide, disodiumhydrogenphosphate, trisodiumphosphate, dipotassiumhydrogenphosphate, tripotassiumphosphate, dilithiumhydrogenphosphate, trilithiumphosphate, diammoniumhydrogenphosphate, and triammoniumphosphate. Alkylating agents capable of producing a hydroxyethylated product suitable for use with the invention include 2-chloroethanol, ethylene oxide, ethylene carbonate, 2-bromoethanol, 2-iodoethanol, and 2-tosylethanol. Acetate ions for use with inventions include sodium, lithium, ammonium and potassium.

Specifically, the process of the invention is detailed in the Examples section of this document.

The following examples illustrate the specific embodiments of the invention described in this document. As would be apparent to skilled artisans, various changes and modifications are possible and are contemplated within the scope of the invention described.

EXAMPLES

Example 1

Preparation of N,N'-bis[2,3-di(2-chloroacetoxy) propyl]-5-(2-chloroacetamido)-2,4,6-triiodoisophthalamide 5-Amino-N,N'-bis (2,3-dihydroxypropyl)-2,4,6-triiodoisophthalamide (84.6 g, 0.12 moles) was dissolved in 172 mL of N,N-dimethylacetamide at 50° C. The solution was cooled to 10° C. and 62 mL (88.09 g, 0.78 moles) of chloroacetyl chloride were added over 30 minutes. The reaction mixture was stirred for 3 hours at 50° C. HPLC analysis of the reaction mixture showed that it contained 99.8% N,N'-bis[2,3-di-(2-chloroacetoxy)propyl]-5-(2-chloroacetamido)-2,4,6-triiodo-isophthalamide. The material was carried forward to Example 2 without further purification.

Example 2

Preparation of N,N'-bis(2,3-dihydroxypropyl)-5-(2-chloroacetamido)-2,4,6-triiodoisophthalamide N,N'-bis[2,3-di(2-chloroacetoxy)propyl]-5-(2-chloroacetamido)-2,4,6-triiodoisophthalamide in N,N-dimethylacetamide, from Example 1, was hydrolyzed by adding 156 mL of 10N sodium hydroxide solution (1.56 moles). Water (100 mL) was then added to the mixture to give a homogeneous solution. 1N Hydrochloric acid(59 mL, 0.59 moles) was added to precipitate the N,N'-bis (2,3-dihydroxypropyl)-5-(2-chloroacetamido)-2,4,6-triiodoisophthalamide. The precipitate was collected and washed with water. The wet product was dried at 60° C. in a vacuum oven to give 81.69 g of product, 88.4% yield. The material was 100% pure by HPLC analysis.

Example 3

Preparation of N,N'-bis[2,3-di(2-chloroacetoxy) propyl]-5-(2-chloroacetamido)-2,4,6-triiodoisophthalamide 5-Amino-N,N'-bis(2,3-dihydroxypropyl)-2,4,6-triiodoisophthalamide (70.5 g, 0.1 moles) was dissolved in 71 mL of N,N-dimethylacetamide at 50° C. Acetonitrile (71 mL) was added to the mixture. Chloroacetyl chloride (52 mL, 73.4 g, 0.65 moles) was added over 30 minutes. The reaction mixture was stirred for 3 hours at 50° C. HPLC analysis of the reaction mixture showed that it contained 98.5% N,N'-bis[2,3-di(2-chloroacetoxy)propyl]-5-(2-chloroacetamido)-2,4,6-triiodoisophthalamide. The material was carried forward to Example 4, without further purification.

Example 4

Preparation of N,N'-bis(2,3-dihydroxypropyl)-5-(2-chloroacetamido)-2,4,6-triiodoisophthalamide N,N'-bis[2,3-di(2-chloroacetoxy)propyl]-5-(2-chloroacetamido)-2,4,6-triiodoisophthalamide in N,N-dimethylacetamide and acetonitrile, from Example 3, was hydrolyzed by adding 130 mL of 10N sodium hydroxide solution (1.3 moles). Water (36 mL) was then added to the mixture to give a homogeneous solution. 1N Hydrochloric acid (100 mL, 0.1 moles) was added to precipitate the N,N'-bis(2,3-dihydroxypropyl)-5-(2-chloroacetamido)-2,4,6-triiodoisophthalamide. The precipitate was collected and washed with water. The wet product was dried at 60° C. in a vacuum oven to give 71.6 g of product, 92.2% yield. The material was 100% pure by HPLC analysis.

Example 5

Preparation of N,N'-Bis(2,3-dihydoxypropyl)-5-[N-(2-hydroxyethyl)-2-chloroacetamido]-2,4,6-triiodoisophthalamide N,N'-Bis(2,3-dihydroxypropyl)-5-chloroaceetamido-2,4,6-triiodoisophthalamide (16.7 g, 0.0214 moles) and sodium chloride (0.5 g; 0.0086 moles) were added to an ethylene oxide (8.85 g, 0.2009 moles) solution in de-ioinizing water (60 mL). The reaction mixture was stirred and heated to 50° C. for 8.5 hours. Hydrochloric acid (0.5N) was added to maintain the pH of the reaction. Initially, when the reaction mixture was a slurry, the pH was maintained at 9.4. After 4 hours, when all the solids have dissolved, the pH was maintained at 8.8. HPLC analysis of the reaction mixture after 8 hours showed that it contained 96.45% of N,N'-bis(2,3-dihydroxypropyl)-5-[N-(2-hydroxyethyl)-2-chloroacetamido]-2,4,6-triiodoisophthalamide. The reaction mixture was acidified to pH 2.5 with 0.5N hydrochloric acid and was stripped to dryness on a rotavapor to give 20.38 g of white solid. The solid was carried forward without further processing.

Example 6

Preparation of N,N'-Bis(2,3-dihydroxypropyl)-5-N-(2-hydroxyethyl)glycolamido-2,4,6-triiodoisophthalamide N,N'-Bis(2,3-dihydroxypropyl)-5-[N-(2-hydroxyethyl)-2-chloroacetamido]-2,4,6-triiodoisophthalamide (4.15 g, 0.01 moles) and anhydrous sodium acetate (3.28 g, 0.08 moles) were dissolved in water. Acetic acid (0.5 mL) was added to adjust the pH of the solution and the solution was heated to reflux. Water (3.5 mL) was added and the mixture was refluxed for 14 hours. HPLC analysis of the reaction mixture showed that it contained 92.6% N,N'-bis(2,3-dihydroxypropyl)-5-N-(2-hydroxyethyl)glycolamido-2,4,6-triiodoisophthalamide. The reaction mixture was carried forward without further processing.

Example 7

Removal of Salts and Other Lower Molecular Weigh Impurities from Crude Ioversol

A column (2.5 cm diameter, 29 cm height) was packed, using the procedure recommended by the manufacturer, with Amberlite XAD-16 resin. Crude ioversol (4.5 g) containing ioversol (45.3%), sodium acetate (40.9%), NaCl (3.2%), ethylene glycol (10.2%) and other organic impurities was dissolved in water (12 mL) and loaded into the XAD-16 column. The column was eluted with water at a flow rate of 3.0 mL per minute. The elution profile was monitored with a conductivity meter for ionic substances and an UV detector at 254 nm for ioversol. When the conductivity, started to increase, fractions were collected (30 mL each). The salts and other lower molecular weight impurities were eluted from the column. The column was then eluted with a mixture of methanol and water (50/50) which cleanly effected dead-sorption of ioversol from the column in 95–99% yield. The XAD-16 column may be re-equilibrated with water for reuse. The isolated ioversol fraction contained less than 5 ppm of ethylene glycol (by HPLC) and were devoid of ionic impurities (by conductivity analyses).

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

| Assay of the Fractions for Ethylene Glycol and Ioversol | | |
|---|---|---|
| Fraction # | Ethylene Glycol ($\mu$g/mL) | Ioversol (mg/mL) |
| 1 | <5 | — |
| 2 | 1500 | — |
| 3 | 3500 | — |
| 4 | 4200 | — |
| 5 | 2800 | — |
| 6 | 750 | — |
| 7 | 89 | — |
| 8 | 23 | — |
| 9 | 19 | — |
| 10 | 21 | — |
| 11 | 24 | — |
| 12 | 25 | — |
| 13 | 23 | — |
| 14 | 20 | — |
| 15 | 16 | — |
| 16 | <5 | 1.33 |
| 17 | <5 | 21.50 |
| 18 | <5 | 9.00 |
| 19 | <5 | 3.11 |
| 20 | <5 | 1.14 |
| 21 | <5 | 0.32 |
| 22 | <5 | 0.12 |
| 23 | <5 | 0.04 |

| HPLC % Composition of Iodinated Compounds in the Fractions | | | | | | |
|---|---|---|---|---|---|---|
| Fraction # | Ioversol | MP-104 | MP-227 | MP-429 | MP-602 | Others |
| 16 | 94.2 | ND | ND | 1.26 | 1.84 | 0.37 |
| 17 | 91.9 | 0.96 | ND | 2.73 | 0.90 | 2.04 |
| 18 | 83.1 | 3.33 | 0.11 | 3.90 | 0.72 | 6.32 |
| 19 | 74.4 | 6.13 | 0.77 | ND | 0.55 | 14.6 |
| 20 | 66.4 | 8.85 | ND | 4.69 | 0.47 | 13.9 |
| 21 | 60.2 | 12.32 | ND | 4.84 | 0.41 | 17.2 |
| 22 | 60.4 | 14.75 | ND | 5.70 | ND | 19.3 |
| 23 | 60.6 | 15.85 | ND | 4.27 | ND | 17.2 |

Ioversol = N,N'-bis(2,3-dihydroxypropyl)-5-N-(2-hydroxyethyl) glycolamido-2,4,6-triiodoisophthalamide
MP-104 = 5-Amino-N,N'-bis(2,3-dihydroxypropyl)-2,4,6-triiodoisophthalamide
MP-227 = 5-Acetamido-N,N'-bis(2,3-dihydroxypropyl)-2,4,6-triiodoisophthalamide
MP-429 = N,N'-bis(2,3-dihydroxypropyl)-5-[2-(hydroxyacetoxy)ethylamino]-2,4,6-triiodoisophthalamide
MP-602 = N,N'-bis(2,3-dihydroxypropyl)-5-glycolamido-2,4,6-triiodoisophthalamide

What is claimed is:

1. A process for producing ioversol comprising:

(a) reacting 5-amino-N,N'-bis(2,3-dihydroxypropyl)-2,4,6-triiodoisopthalamide with chloroacetyl chloride in a polar aprotic solvent or combinations thereof to produce N,N'-bis[2,3-di(2-chloroacetoxy)propyl]-5-(2-chloroacetamido)-2,4,6-triiodoisophthalamide;

(b) reacting the product of (a) with a base to produce N,N'-bis(2,3-dihydroxypropyl)-5-(2-chloroacetamido)-2,4,6-triiodoisopthalamide;

(c) reacting the product of (b) with an alkylating agent capable of producing a hydroxyethylated product in the presence of a base and water to produce N,N'-bis(2,3-dihydroxypropyl)-5-[N-(2-hydroxyethyl)(2-chloroacetamido)]-2,4,6-triiodoisopthalamide; and (d) reacting the product of (c) in water and acetate ions to produce ioversol.

2. The process of claim 1 wherein the polar aprotic solvent is selected from dimethylacetamide, acetonitrile, dimethylsulfoxide, dimethylformamide, tetrahydrofuran, dimethoxyethane, dioxane, or mixtures thereof.

3. The process of claim 2 wherein the polar aprotic solvent is N,N-dimethylacetamide.

4. The process of claim 2 wherein the polar aprotic solvent is N,N-dimethylacetamide and acetonitrile.

5. The process of claim 1 wherein the alkylating agent in (c) is selected from the group consisting of 2-chloroethanol, ethylene oxide, ethylene carbonate, 2-bromoethanol, 2-iodbethanol and 2-tosylethanol.

6. The process of claim 5 wherein the alkylating agent is ethylene oxide.

7. The process of claim 1 wherein the base in (c) is selected from sodium hydroxide, lithium hydroxide, ammonium hydroxide, potassium hydroxide, disodiumnydrogenphosphate, trisodiumphosphate, dipotassiumnhydrogenphosphate, tripotassiumphosphate, dilithiumhydrogenphosphate, trilithiumphosphate, diammoniumhydrogenphosphate, and triammoniumphosphate.

8. The process of claim 7 wherein the base is sodium hydroxide.

9. A process for producing ioversol comprising:
   (a) reacting 5-amino-N,N'-bis(2,3-dihydroxypropyl)-2,4,6-triiodoisopthalamide with chloroacetyl chloride in N,N-dimethylacetamide to produce N,N'-bis[2,3-di(2-chloroacetoxy)propyl]-5-(2-chloroacetamido)-2,4,6-triiodoisophthalamide;
   (b) reacting the product of (a) with sodium hydroxide to produce N,N'-bis(2,3-dihydroxypropyl)-5-(2-chloroacetamido)-2,4,6-triiodoisopthalamide;
   (c) reacting the product of (b) with sodium hydroxide, water, and ethylene oxide, to produce N,N'-bis(2,3-dihydroxypropyl)-5-glycolamido-2,4,6-triiodoisopthalamide; and
   (d) reacting the product of (c) in water and sodium acetate to produce ioversol.

10. A process for producing ioversol comprising:
   (a) reacting 5-amino-N,N'-bis(2,3-dihydroxypropyl)-2,4,6-triiodoisopthalamide with chloroacetyl chloride in N,N-dimethylacetamide and acetonitrile, to produce N,N'-bis[2,3-di(2-chloroacetoxy)propyl]-5-(2-chloroacetamido)-2,4,6-triiodoisophthalamide;
   (b) reacting the product of (a) with sodium hydroxides to produce N,N'-bis(2,3-dihydroxypropyl)-5-(2-chloroacetamido)-2,4,6-triiodoisopthalamide;
   (c) reacting the product of (b) with sodium hydroxide, water, and ethylene oxide, to produce N,N'-bis(2,3-dihydroxypropyl)-5-[N-(2-hydroxyethyl)(2-chloroacetamido)]-2,4,6-triiodoisopthalamide; and
   (d) reacting the product of (c) in water and sodium acetate to produce ioversol.

* * * * *